(12) United States Patent
Pieper et al.

(10) Patent No.: US 11,471,548 B2
(45) Date of Patent: Oct. 18, 2022

(54) COMPOSITION FOR AIR FRESHENER SYSTEM

(71) Applicant: Aeron Lifestyle Technology, Inc., Fairfield, IA (US)

(72) Inventors: Joseph Pieper, Garner, IA (US); Monica Herr Hadley, Fairfield, IA (US)

(73) Assignee: Aeron Lifestyle Technology, Inc., Fairfield, IA (US)

( * ) Notice: Subject to any disclaimer, the term of this patent is extended or adjusted under 35 U.S.C. 154(b) by 127 days.

(21) Appl. No.: 17/180,286

(22) Filed: Feb. 19, 2021

(65) Prior Publication Data

US 2022/0265884 A1 Aug. 25, 2022

(51) Int. Cl.
*A61L 9/013* (2006.01)
*A61L 9/12* (2006.01)

(52) U.S. Cl.
CPC ............... *A61L 9/013* (2013.01); *A61L 9/127* (2013.01)

(58) Field of Classification Search
CPC .................................. A61L 9/013; A61L 9/127
See application file for complete search history.

(56) References Cited

U.S. PATENT DOCUMENTS

| 4,809,912 A * | 3/1989 | Santini ...................... A61L 9/12 239/57 |
| 10,695,273 B2 * | 6/2020 | Eppler ................... A61Q 19/10 |
| 2017/0151363 A1 * | 6/2017 | Baxter ................ B05B 11/0078 |
| 2019/0054008 A1 * | 2/2019 | Chan ...................... A61Q 19/00 |

* cited by examiner

*Primary Examiner* — Pamela H Weiss
(74) *Attorney, Agent, or Firm* — Zarley Law Firm PLC

(57) ABSTRACT

A composition for an air freshener system including a 100% natural mixture of essential oil and one or more diluents that is adapted to have a longevity of between fifteen to forty days and include a flash point for the blend that is high enough that the blend remains effective for the desired period of time and slows the consumption of the essential oil and provides a consistent weight loss over the course of the air freshener system's consumption of the oil mixture.

5 Claims, 4 Drawing Sheets

COMPOSITION FOR AIR FRESHENER SYSTEM

BACKGROUND OF THE INVENTION

The present invention is directed to a composition for an air freshener system and more particularly a 100% natural liquid composition for an electric air freshener system.

Air freshening compositions are well known in the art. While these compositions are useful some compositions, and particularly those used with electric air freshener systems, do not have an acceptable longevity, they do not have a flash point within an acceptable range to be effective, or they are cost prohibitive. In other words, the composition can burn off in just a few days or they can clog the wick so that the system is ineffective and the composition does not burn off. Also, some compositions do not have a slow enough usage rate and do not have a consistent weight loss over the course of the air freshener's consumption of the oil mixture. Therefore, there is a need in the art for a 100% natural composition that improves upon these deficiencies.

An objective of the present invention is to provide a composition for an air freshener system that slows the usage rate of essential oils and has a more consistent weight loss over the course of the consumption of the oil mixture by the air freshener system.

Another objective of the present invention is to provide a composition for an air freshener system that is cost effective to manufacture and use.

These and other objectives will be known by one skilled in the art based upon the following written description, drawings, and claims.

SUMMARY OF THE INVENTION

A composition for an air freshener/fragrance system includes a mixture of essential oils and two or more diluents adapted to have a longevity of between fifteen to forty days and preferably eighteen to twenty-one days. The two or more diluents are adapted to slow the usage rate of the essential oil and provide a consistent weight loss over the course of the air freshener system's consumption of the oil mixture.

Preferably the diluents include a combination of Hemisqualane and Squalane and is adapted for use with a wick wrapped in nylon. The preferred mixture includes 40 to 55% Hemisqualane, 0.1 to 5% Squalane, and 40 to 60% essential oils.

DETAILED DESCRIPTION

Figure 1:
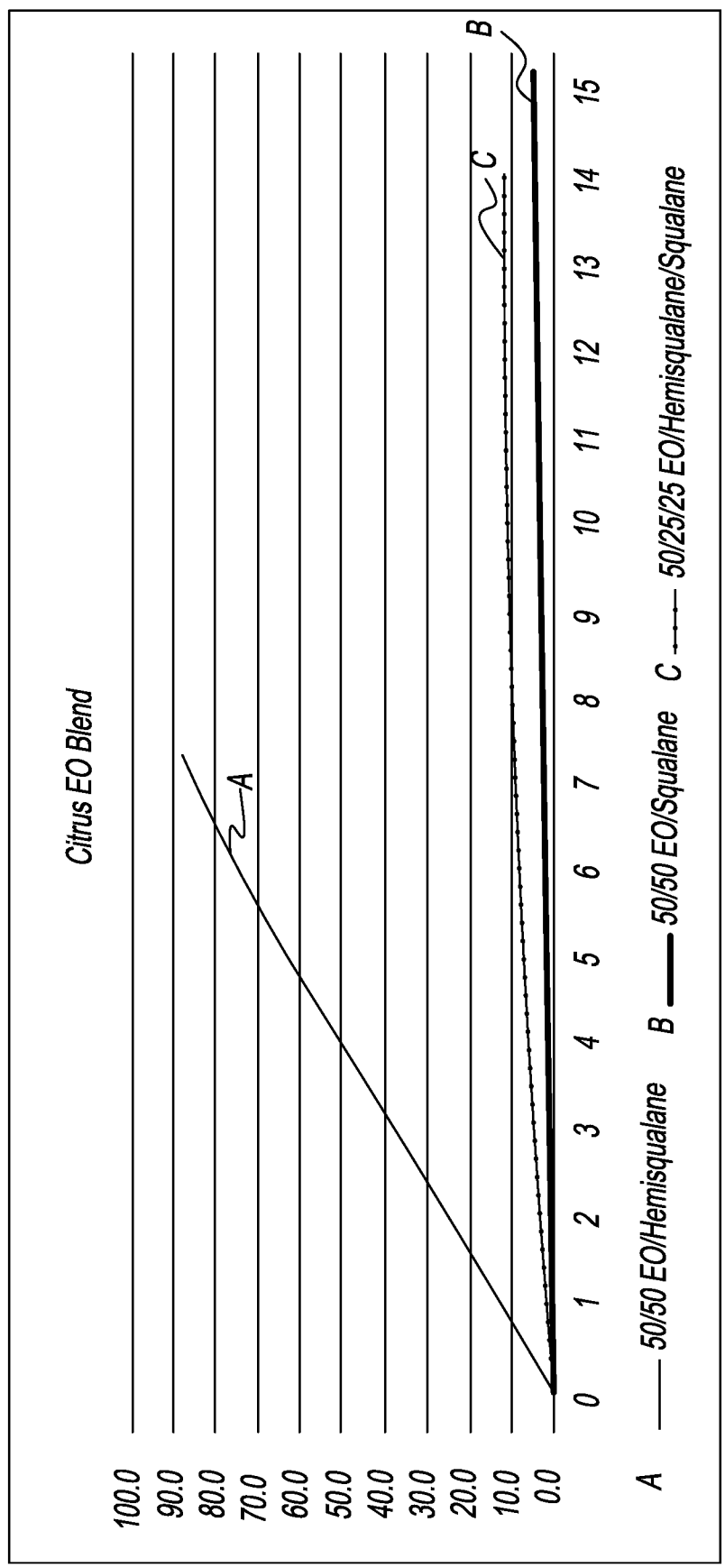
FIG. 1 is a chart showing the consumption rate of different mixtures.

A composition 10 for an air freshener system 12 includes a mixture or blend 14 of essential oil 16 and one or more diluents 18 adapted to have a longevity of between fifteen to forty days and optimally eighteen to twenty-one days. Longevity is defined as consumption of ninety percent or more of the starting weight of the blend. Thus, the flash point of the blend 14 needs to be in the "Goldilocks zone"—that is not too high and not too low, so that the blend remains effective for the desired time period. A majority of known blends tend to eventually clog a wick halting the consumption of the fragrance. Also required is that the mixture is of all-natural materials.

Figure 3:
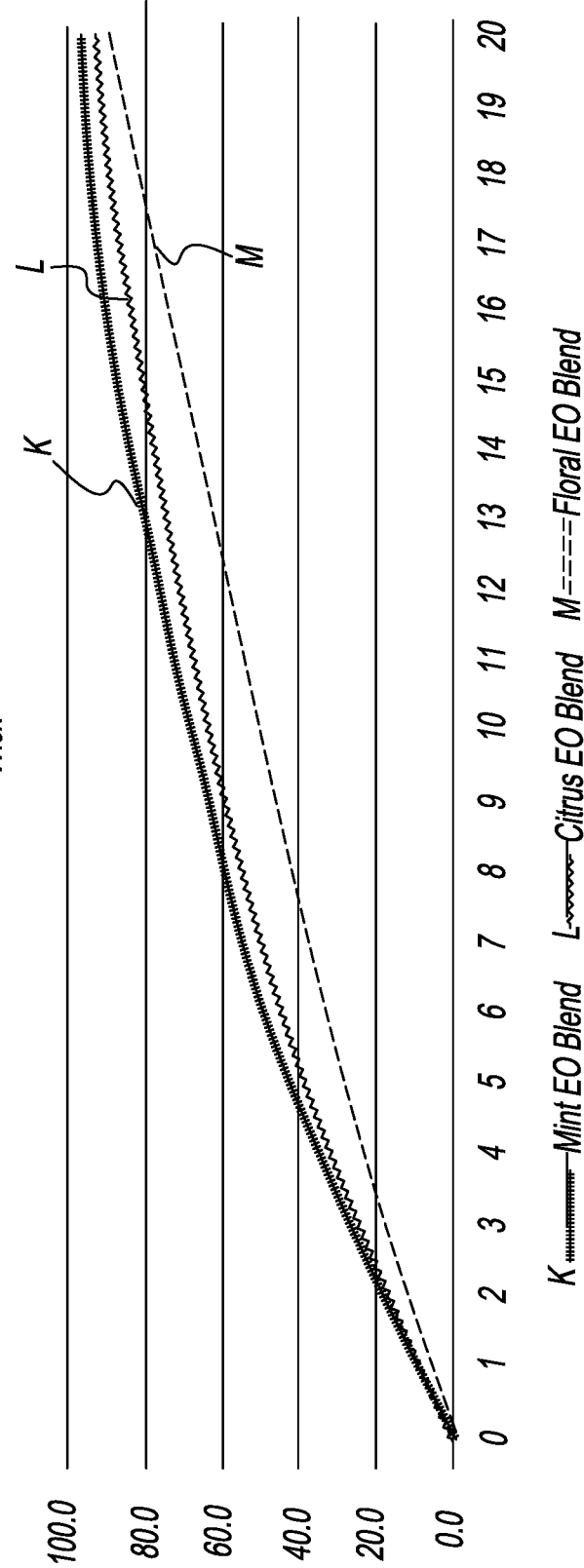
FIG. 3 is a chart showing the consumption rate of different mixtures used with a nylon wrapped wick.
Figure 4:
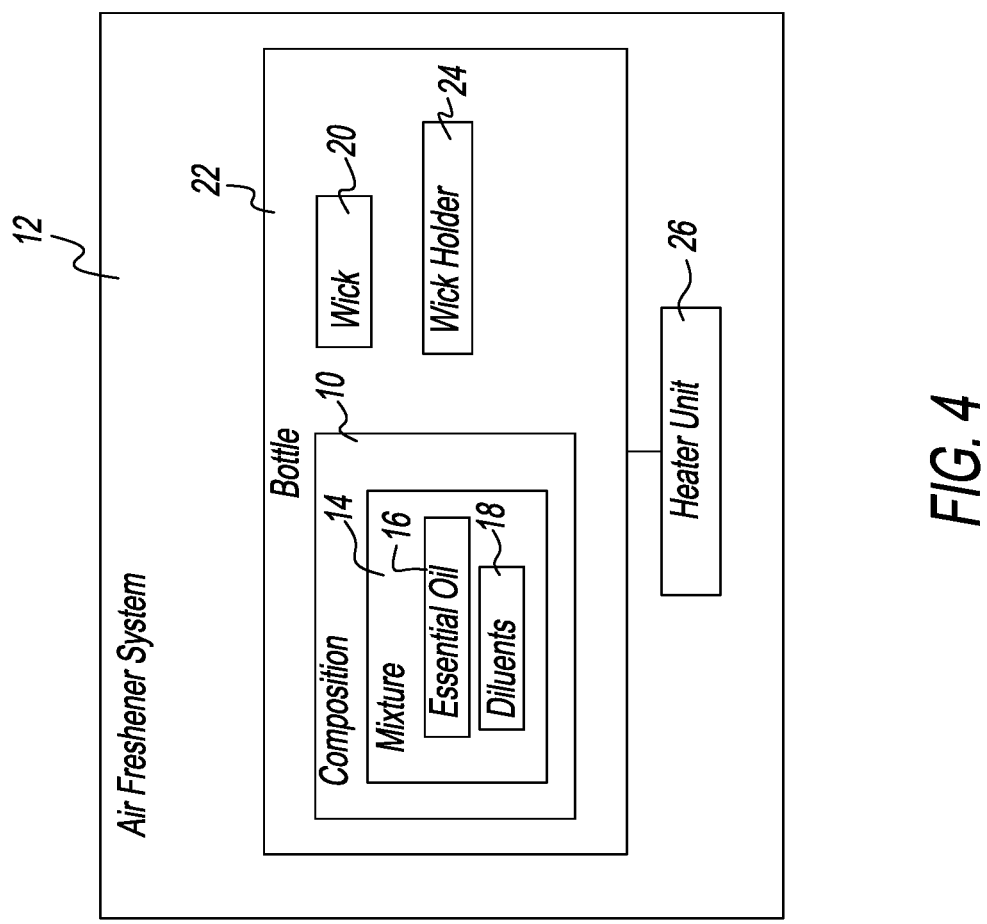
FIG. 4 is a schematic view of an air freshener system.

The diluents 18 are of any all-natural type that slows the usage rate of the essential oil 16 and provides a consistent weight loss over the course of the life of the mixture 14. In a preferred embodiment, a combination of Hemisqualane and Squalane meets the desired requirements. Used alone with the essential oil 16, Squalane only consumed 6% of the blend 14 after fifteen days. In contrast, Hemisqualane consumed the blend 14 in only seven to eight days. The blending of the Squalane and the Hemisqualane produced better results but the consumption rate was still faster than desired. However, when used in combination with a wick 20 wrapped in nylon the consumption rate fell within the desired time window and was also cost effective, as shown in FIG. 3.

Using the blend 14 with a non-nylon wrapped wick resulted in reduced effectiveness and a discolored and deformed wick. While the discolored and deformed wick was not hazardous to a consumer, the wick was not visually appealing. The nylon wrapped wick 20 improved results and prevented deformation and excess discoloration.

Figure 2:
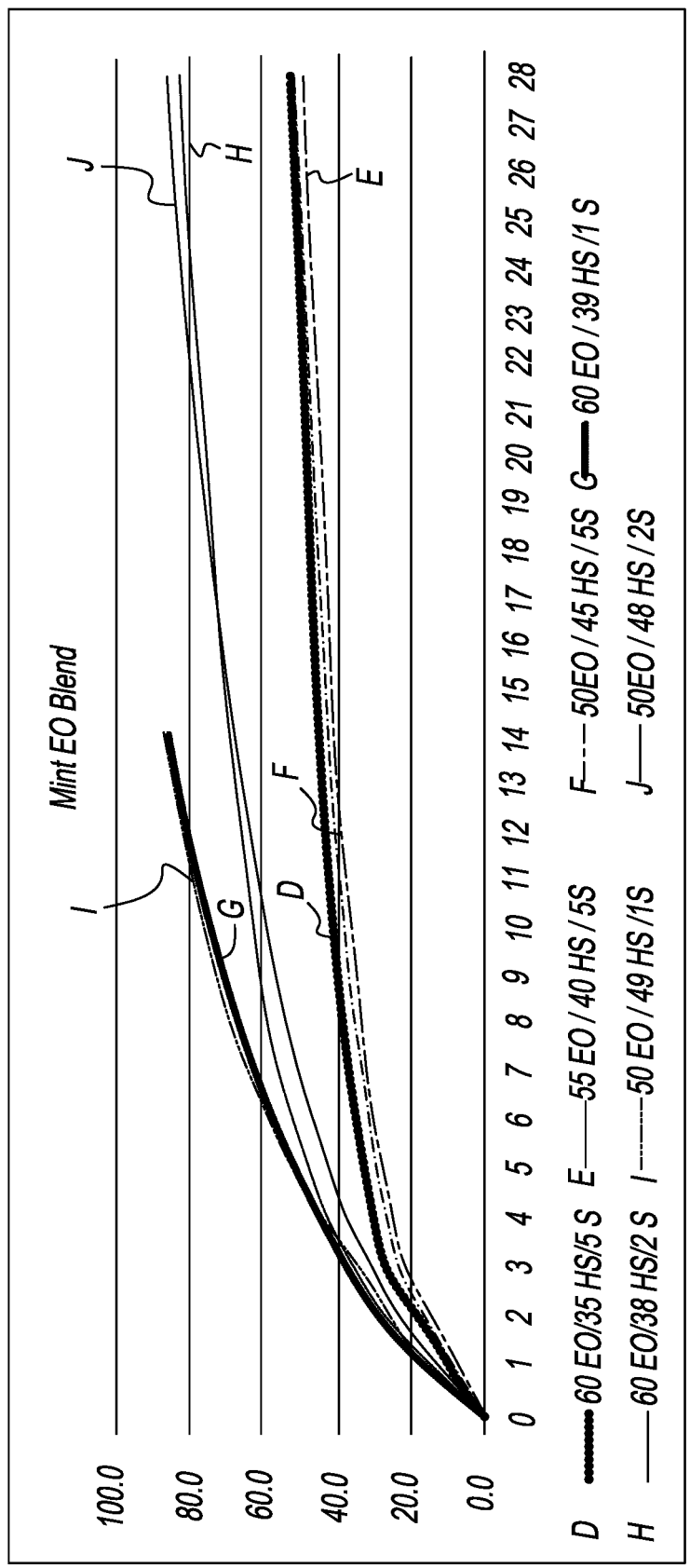
FIG. 2 is a chart showing the consumption rate of different mixtures.

In operation, the composition 10 is added to a tared bottle 22. A wick holder 24 and the wick 20 are added to the bottle 22 and the assembled bottle is inserted into a heater unit 26 such as those adapted for use in a 120-volt wall plug. FIG. 1 shows testing results for a 50/50 blend of Hemisqualane and essential oil in line A, the same 50/50 split with Squalane in line B, and a 50/25/25 split between essential oil and the two diluents 18 in line C. FIG. 2 shows test results for various blends in lines D through J. Finally, FIG. 3 shows use of the composition 10 that included different types of essential oils in lines K through M. Best results were achieved by using a blend 14 of 40 to 55% Hemisqualane, 0.1 to 5% Squalane, and 40 to 60% essential oil 16.

Therefore, a composition 10 provides a flash point high enough so that the mixture 14 will have a desired longevity, but not too high that the mixture 14 becomes ineffective, and consequently improves upon the art.

From the above discussion and accompanying figures and claims it will be appreciated that the composition 10 offers many advantages over the prior art. It will be appreciated further by those skilled in the art that other various modifications could be made to the device without parting from the spirit and scope of this invention. All such modifications and changes fall within the scope of the claims and are intended to be covered thereby. It should be understood that the examples and embodiments described herein are for illustrative purposes only and that various modifications or changes in the light thereof will be suggested to persons skilled in the art and are to be included in the spirit and purview of this application.

What is claimed is:

1. A composition for an air freshener system, comprising:
   a 100% natural mixture of essential oils and at least two diluents adapted to have a longevity of between fifteen to forty days; and
   wherein the at least two diluents include a combination of Hemisqualane and Squalane.

2. The composition of claim 1 further comprising a mixture of essential oils and at least one diluent of the at least two diluents is adapted to have a longevity of between eighteen and twenty-one days.

3. The composition of claim 1 wherein at least one of the at least two diluents is adapted to slow the usage rate of the essential oil and provides a consistent weight loss over the course of the air freshener system's consumption of the oil mixture.

4. The composition of claim 1 wherein the mixture is adapted for use with a wick wrapped in nylon.

5. The composition of claim 1 wherein the mixture includes 40% to 55% Hemisqualane, 01% to 5% Squalane, and 40% to 60% essential oils.

\* \* \* \* \*